(12) United States Patent
Sugiyama

(10) Patent No.: US 7,807,367 B2
(45) Date of Patent: Oct. 5, 2010

(54) ENZYMATIC FLUOROMETRIC ASSAY FOR CAMP AND ADENYLATE CYCLASE AND KITS THEREFOR

(75) Inventor: Atsushi Sugiyama, Higashiyatsushiro-gun (JP)

(73) Assignee: Fuso Pharmaceutical Industries, Ltd., Osaka-shi (JP)

( * ) Notice: Subject to any disclaimer, the term of this patent is extended or adjusted under 35 U.S.C. 154(b) by 820 days.

(21) Appl. No.: 11/785,611

(22) Filed: Apr. 19, 2007

(65) Prior Publication Data

US 2007/0190589 A1 Aug. 16, 2007

Related U.S. Application Data

(62) Division of application No. 10/807,169, filed on Mar. 24, 2004, now Pat. No. 7,247,435, which is a division of application No. 09/926,138, filed as application No. PCT/JP00/01494 on Mar. 13, 2000, now Pat. No. 6,762,026.

(30) Foreign Application Priority Data

Mar. 18, 1999 (JP) ................. 11-073690

(51) Int. Cl.
*C12Q 1/68* (2006.01)
(52) U.S. Cl. .......................................... 435/6
(58) Field of Classification Search ........................ None
See application file for complete search history.

(56) References Cited

U.S. PATENT DOCUMENTS

| | | |
|---|---|---|
| 5,618,665 A | 4/1997 | Lurie et al. |
| 5,891,702 A | 4/1999 | Sakakibara et al. |
| 6,762,026 B1 | 7/2004 | Sugiyama |

OTHER PUBLICATIONS

Bergstrand, H., et al., The Journal of Biological Chemistry, vol. 253, No. 6, Mar. 25, 1978, pp. 1881-1891.
Breckenridge, B. M., Biochemistry, Proc. N.A.S., 1964, pp. 1580-1586.
Omburo, G.A., et al., Archives of Biochemistry and Biophysics, Vo. 323, No. 1, Oct. 20, 1995, pp. 1-5.
Saegusa, Y., et al., Journal of Clinical Laboratory Analysis, vol. 14, Feb. 1, 2000, pp. 115-119.
Sawada, N., et al., Journal of Clinical Laboratory Analysis, vol. 13, 1999, pp. 90-94.
Sugiyama, A., et al., Analytical Biochemistry, vol. 218, 1994, pp. 20-25.
Sugiyama, A., et al., Analytical Biochemistry, vol. 225, 1995, pp. 368-371.
Sugiyama, A., et al., Journal of Clinical Laboratory Analysis, vol. 8, 1994, pp. 437-442.
Sugiyama, A., et al., Journal of Clinical Laboratory Analysis, vol. 14, 2000, pp. 48-52.
Wiegn, P., et al., Analytical Biochemistry, vol. 208, 1993, pp. 217-222.

*Primary Examiner*—Sandra Saucier
(74) *Attorney, Agent, or Firm*—Bacon & Thomas, PLLC

(57) ABSTRACT

The present invention relates to a method for quickly determining cAMP content or an adenylate cyclase activity in a biological sample containing non-cyclic adenine nucleotides without the use of radioactive agents.

Particularly, the present invention provides a method of determining CAMP content or an adenylate cyclase activity in a biological sample containing non-cyclic adenine nucleotides selected from the group consisting of cAMP produced by endogenous adenylate cyclase, and AMP, ATP, ADP and a mixture thereof, which comprises (1) combining a biological sample with effective amounts of apyrase, adenosine deaminase and alkaline phosphatase to enzymatically remove non-cyclic adenine nucleotides other than cAMP, and glucose-6-phosphate in the sample; (2) enzymatically converting cAMP into AMP; (3) determining an amount of AMP without the use of radioactive agents, and a kit to carry out the method.

2 Claims, 4 Drawing Sheets

ENZYMATIC FLUOROMETRIC ASSAY FOR CAMP AND ADENYLATE CYCLASE AND KITS THEREFOR

CROSS-REFERENCE TO RELATED APPLICATIONS

This is a divisional of U.S. application Ser. No. 10/807,169, filed Mar. 24, 2004, which in turn is a division of U.S. application Ser. No. 09/926,138, filed Sep. 10, 2001, which in turn is a 371 of PCT/JP00/01494, filed Mar. 13, 2000.

TECHNICAL FIELD

The present invention provides a method of determining cAMP content or an adenylate cyclase activity in a biological sample containing non-cyclic adenine nucleotides selected from the group consisting of cAMP produced from ATP by endogenous adenylate cyclase (cyclic adenosine-3',5'-monophosphate), ATP (adenosine-triphosphate), ADP (adenosine-diphosphate) and a mixture thereof without the use of radioactive agents. More particularly, the invention relates to a method which comprises: (1) combining a biological sample with effective amounts of apyrase, adenosine deaminase and alkaline-phosphatase to enzymatically remove non-cyclic adenine nucleotides other than cAMP, and glucose-6-phosphate in the sample; (2) enzymatically converting cAMP into AMP; (3) determining an amount of AMP without the use of radioactive agents.

Adenylate cyclase (adenylyl cyclase, adenylate cyclase, EC4.6.1.1) is an enzyme catalyzing the conversion:

ATP→cAMP in the presence of $Mg^{2+}$ or $Mn^{2+}$.

Adenylate cyclase exists locally on cell membranes and plays a critical role as a signal transduction cascade of a number of fundamental hormones and neurotransmitters.

For example, measurement of adenylate cyclase activity has been employed to study the altered physiology exhibited by transplanted human hearts and in congestive heart failure. See M. R. Bristow et al., *New Engl. J. Med.,* 307, 205 (1982); K. G. Lurie et al., *J. Thorac. Cardiovasc. Surg.,* 86, 195 (1983).

Adenylate cyclase activity can be determined by monitoring the changes of cAMP content synthesized from ATP by the catalytic action of adenylate cyclase.

However, a more clear elucidation of the biological role of adenylate cyclase has been limited by the difficulty in monitoring accurately changes in the tissue level of cAMP.

cAMP (cyclic adenosine-3',5'-monophosphate) was found as a factor which intermediates blood sugar rising action of adrenaline and glucagon in liver cells. [E. W. Sutherland et al., *J. Am. Chem. Soc.,* 79, 3608 (1957)]. And also CAMP was found to intermediate actions of hormones such as adrenocorticotropin (ACTH), luteinizing hormone (LH), tyrosine stimulating hormone (TSH) and parathyroid hormone (PTH) or physiological active substances such as prostaglandin. Thus, when peptide hormones or active amines have been secreted and have reached at target cells, cAMP transfers information for them to proceed enzymatic reactions, that is, plays a role of a second messenger.

cAMP is synthesized from ATP by adenylate cyclase located on membranes in the living body and decomposed by phosphodiesterase into 5'-AMP. cAMP is present widely in bacteria or animals but the concentration of cAMP is extremely low (a stationary concentration is 0.1-1 nmol/g wet weight). As an assay of cAMP, an assay using cAMP binding protein or radioimmunoassay is conveniently employed. The cAMP content depends on eutrophy, proliferation, differentiation, adaptation of cells and changes in sensitivity.

Measurement of cAMP in a wide variety of mammalian and non-mammalian tissue and fluids provides a useful way to assess cell viability, endocrine hormonal axis function, adenylate cyclase activity and phosphodiesterase activity. In addition, measurement of cAMP can be used to evaluate the activity of a number of signal transproduction proteins, including, but not limited to, the family of G proteins (guanine-nucleotide binding protein) which play a major role in signal transduction, ribosomal protein synthesis, translocation of nascent proteins and other important cellular functions. Bourne et al., *Nature,* 348, 125 (1990).

Furthermore, measurement of cAMP may be used in evaluating other endogenous and exogenous compounds (for example, nitrous oxide) which may alter the level of cyclic nucleotides in a particular cell, tissue, organ or body fluid.

Many hormones use cAMP as a second messenger including, but not limited to: epinephrine, norepinephrine, adrenocorticotropin (ACTH), vasopression, glucagon, thyroxine, and thyroid-stimulating and melanocyte-stimulating hormones which are some of the principle regulatory hormones/proteins in the living organism. The activity of all of these hormones and regulators can be measured in tissues, serum, body fluids, and in all cell cultures (cells and medium) using the method for cAMP of the present invention. Measurement of these hormones is performed in a wide variety of disease states where hormonal imbalance may lead to specific pathology.

Once a hormone or regulatory protein interacts with a specific receptor, the second messenger, in this case, cAMP, is produced through a cascade of biochemical events. The production of cAMP can also be specifically inhibited in some cases by hormones which use a decrease in cAMP as part of the specific hormonal signal-transduction pathway. The result of this regulatory protein or hormone and receptor interaction can be, but is not limited to, (1) an alteration in cell permeability secondary, for example, to changes in ion channels, (2) and alteration in the rate of enzyme catalyzed reactions sensitive to the concentration of cAMP, and (3) an alteration in the rate of protein synthesis including the synthesis and degradation of other enzymes. a content of cAMP can be used to directly and indirectly monitor the consequences after interacting a hormone or regulatory protein with a receptor.

Specifically, cAMP can be measured in urine or blood for use as a marker for drug levels, like aminophylline or theophylline which stimulate the adrenergic nervous system by preventing the breakdown of endogenous cAMP. Measurement of cAMP in cell cultures can be used to assess specific hormones, regulatory protein and drugs where cAMP represents a vital link in the signal transduction process.

cAMP can also be used to assess cell viability and stability by studying cells in the absence or presence of a specific hormone or regulatory protein. For example, measurement of cAMP in liver cells (hepatocyte) by glucagon, can be used to assess hepatocyte viability. This may be useful, for example, in organ and/or cell transplantation, for example heart, liver, lung, kidney, pancreas, skin and brain cell transplantation.

Measurement of the responsiveness of cells from biopsy samples after activation by a wide variety of hormones, regulatory proteins and drug which either increase or decrease cellular cAMP levels, can be used as a way to specifically assess cell function.

A specific clinical example is the use of cAMP measurement in cardiac biopsies to assess the responsiveness of myocardium. Cardiomyopathic heart cells do not respond with the same rise in cAMP content after β-adrenergic stimulation as normal heart cells. The diagnosis of the severity of the heart disease and the efficacy of some drugs, such as β-adrenergic blockers and angiotensin converting enzyme inhibitors, can be made comparing the responsiveness of biopsy samples from normal hearts to cardiomyopathic hearts. Measurement of basal and/or stimulated levels of adenylate cyclase activity or cAMP in blood cells can be used to guide therapy in such patients. In addition, release of cAMP either intracellarly or into the arterial or venous circulation can be used as an indicator of the response of an organ and/or tissue to a variety of different physiologic and nonphysiologic stresses such as ischemia, hypoxia, or drug or hormonal stimulation. Tissue or body fluid levels of cAMP can be measured in nearly ever mammalian cell or body fluid, including blood cells and platelets, with this approach. In some tissues, cAMP levels can be measured in response to specific stimulators as an index on oncogenicity and/or invasiveness, in the case of samples of potentially tumorous cells. In other cases, measurement of cAMP can be used to determine the effectiveness of specific therapies which may alter cAMP synthesis or degradation.

As described above, cAMP plays an important role as a second messenger in information transfer in cells as well as has also various physiological functions. It is significant in fields of basic and clinical medicine to measure cAMP synthesized from ATP by a catalytic action of adenylate cyclase in order to determine activity of adenylate cyclase or elucidate behavior of cAMP.

BACKGROUND ART

Measurement of adenylate cyclase activity is carried out by quantitative determination of cAMP produced from ATP as a substrate. Methods for measurement of cAMP are grouped into two methods using as a substrate (1) labeled ATP and (2) non-labeled ATP.

In the method using labeled ATP as a substrate (1), using ATP labeled by a radioactive element, for example, [α-$^{32}$P] ATP, as a substrate, and cAMP ([$^{32}$P] cAMP) generated from radioactively labeled ATP is separated and determined. See Y. Salomon et al., *Anal. Biochem.*, 58, 541 (1974; R. A. Johnson et al., *In Method in Enzymology*, 195, 3 (1991)). The method employs sequential affinity chromatography with ionic exchange resin and aluminum oxide columns for separation of [$^{32}$P] cAMP from [α-$^{32}$P] ATP.

Although this method is sensitive, it relies upon dangerously and costly radioactively labeled compounds.

On the other hands, the methods using non-labeled ATP are classified into (1) radioimmunoassay wherein radioactively labeled cAMP is subjected to antigen-antibody reaction competitively with anti-serum including cAMP generated from non-labeled ATP and then radioactivity of binding antibody is assayed to determine cAMP content, and (2) protein-binding assay wherein radioactivity of $^3$H-cAMP bound with cAMP-dependent protein kinds is measured using specific binding between cAMP-dependent protein kinase and cAMP. See A. G. Gilman et al., *Proc. Natl. Acad. Sci. USA*, 67, 305 (1970).

The method using the substrate non-labeled ATP can not compensate decomposition of cAMP by cyclic nucleotide phosphodiesterase and therefore the method is not appropriate for samples including strong phosphodiesterase activity.

Given the safety and environmental concerns, the use of radioactive materials should be avoided. A need exists for a highly sensitive non-radioactive assay to measure adenylate cyclase activity and cAMP as an index of adenylate cyclase activity.

However, it is very difficult to determine cAMP without using radioactive compounds because of the extremely low concentration of cAMP in most mammalian issues. In addition, since non-cyclic adenine nucleotides such as cAMP, ADP and ATP in a biological sample are present in several hundred to several hundred thousand times the concentration of cAMP and also those chemical structures are similar to the that of cAMP, they act as interfering substances in assay of cAMP. Particularly, ATP is present in one hundred million times the concentration of cAMP and therefore it is substantially impossible to exactly determine cAMP without complete removal of endogenous ATP.

On the other hand, cAMP is converted into AMP by action of phosphodiesterase. An assay for AMP without radioactive compounds has been disclosed. Lowry et al. have developed a sensitive assay based on the fluorescence of reduced pyridine nucleotide. See O. H. Lowry et al., *A Flexible System of Enzymatic Analysis*, Harcourt Brace Jovanovich, New York (1972); F. M. Matschinsky et al., *J. Histochem. Cytochem.*, 16, 29 (1968). The assay depends on it that absorbency of reduced nicotinamide adenine dinucleotide phosphate (NADPH) at 340 nm is 0.617 per 0.1 mmol and an absolute concentration of NADPH is calculated on absorbency of a sample.

An assay for AMP is disclosed which depends upon the stimulatory effects of AMP on glycogen phosphorylase, the enzyme that converts glycogen into glucose-1-phosphate in the presence of inorganic phosphate ($P_i$). See E. Helmrich et al., *Biochemistry*, 52, 647 (1964); ibid., 51, 131 (1964); M. Trus et al., *Diabetes*, 29, 1 (1980). According to the method, glycogen phosphorylase activity is determined by an amount of glucose-1-phosphate generated from glycogen and AMP can be assayed using the glycogen phosphorylase activity as an index. Lurie also have developed a sensitive assay for AMP. See K. Lurie et al., *Am. J. Physiol.*, 253, H662 (1987).

A method to increase the analytical sensitivity and specificity for cAMP or adenylate cyclase have employed enzymic degradatiom of non-cyclic adenine nucleotides or their removal by chromatography. See N. D. Goldberg et al., *Anal. Biochem.* 28, 523 (1969); B. Mcl. Breckenridge, *Proc. Natl. Acad. Sci. USA*, 52, 1580 (1964).

In the conventional analysis, since interfering endogenous ADP or ATP could not be completely removed, it has been considered that measurement of cAMP should be impossible. Therefore, there has been substantially no method for highly sensitive measurement of cAMP content and adenylate cyclase activity based on the amount of cAMP without using radioactive substances.

From a completely different point of view, the inventor and others previously attempted to develop assays for adenylate cyclase activity and cAMP and as a results of an intensive study, they had found a method for highly sensitive measurement of cAMP content and adenylate cyclase activity based on the amount of cAMP with using only enzymatic and chemical reactions, which comprises removing selectively interfering substances, endogenous non-cyclic adenine nucleotides, such as ATP, ADP and the like using enzymes, converting AMP into ATP, converting ATP into glucose-6-phosphate through fructose-6-phosphate, converting NADPH, determining NADPH concentration and correlating with cAMP concentration (WO94/17198).

According to the method, cAMP at an amount of µg order in a biological sample can be strictly measured at a level of pmol or fmol. See A. Sugiyama et al., *Anal. Biochem.*, 218, 20 (1994); A. Sugiyama et al., *J. Clin. Lab.*, 8, 437 (1994); A. Sugiyama et al., *Anal. Biochem.*, 225, 368 (1995); A. Sugiyama et al., *Yamanashi Med. J.*, 10, 11 (1995).

The reaction schemes of the conventional method above are described below.

Stage 1: Cleaning Reactions
(Removal of endogenous non-cycle nucleotides and endogenous glucose-6-phosphate)

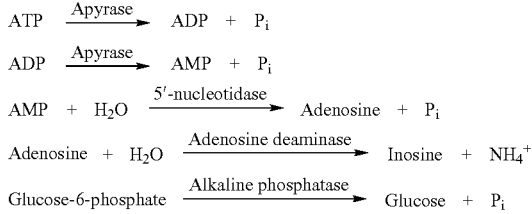

Stage 2: Conversion Reaction 1
(Conversion of cAMP to AMP)

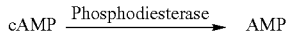

Stage 3: Conversion Reactions 2
(Conversion of AMP to ATP)

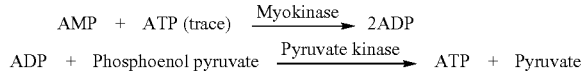

Stage 4: Amplification by ATP-ADP Cycling Reactions
(Assay sensitivity is amplified by 6000-10000 times)

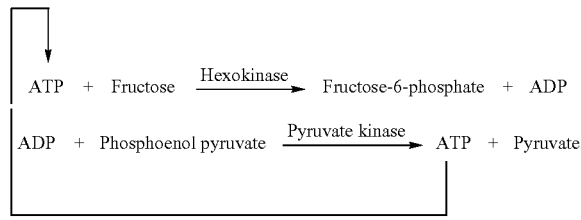

Stage 5: Detection Reactions
(Immunophotometric assay of NADPH)

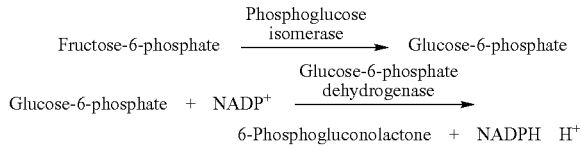

The method as stated above was very excellent as a method for quantitative analysis in a principle of methodology and theoretically correct. However the method takes long time for a cleaning reaction or a reaction mixture gets cloudy when an enzyme has been deactivated by heating after a cycle reaction.

DISCLOSURE OF INVENTION

The present invention has been accomplished as a result of intensive study for development of a simple and fast method for determining cAMP and adenylate cyclase without radioactive substances.

The present invention has improved on the methods of determining adenylate cyclase activity and quantitative analysis for cAMP with enzymatic reactions and fluorescence intensity which the inventor and others previously developed (WO94/17198). That is, (1) in Cleaning Reactions by deleting of 5'-nuleotidase from the enzymes to be used, 1 hour of the reaction period can be extremely shortened to from 5 to 10 minutes; (2) in Cycling Reactions, enzymes used are deactivated by removing $Mg^{2+}$ with a chelating agent such as EDTA, instead of heating. The reaction mixture does not get cloudy and accuracy of Detecting Reaction on the next step is improved; (3) Converting Reaction is changed to 1 step reaction from conventional 2 steps converting reactions. The operation can be simpler; and (4) the concentrations of reaction agents used in Detecting Reactions were reviewed to optimize in the present method. By these improvements, an enzymatic fluorometric assay or a spectrophotometric assay in which cAMP and adenylate cyclase corresponding to cAMP are determined quickly and in high sensitivity could be provided.

Incidentally, as described below, the present method can be used for measurement of guanine regulatory proteins and cAMP specific phosphodiesterase.

The reactions used in the present method for determining cAMP are shown below.

Step 1 - Cleaning Reactions
(Removal of endogenous non-cycle nucleotides and endogenous glucose-6-phosphate)

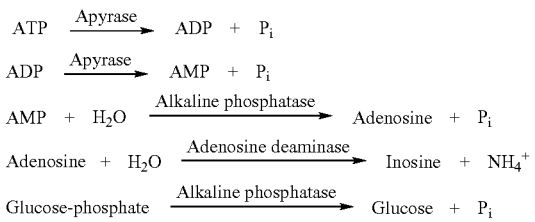

Step 1 - Optional Cleaning Reactions 1
(Removal of fructose-6-phosphate)

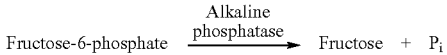

Step 1 - Optional Cleaning Reactions 2
(Removal of endogenous glycogen in a physiological sample)

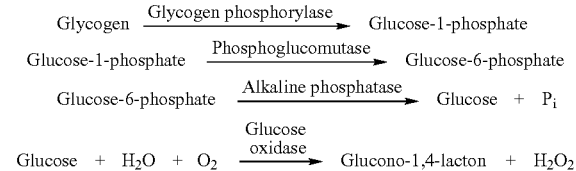

Step 2 - Converting Reaction
(Conversion to AMP)

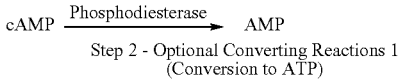

Step 2 - Optional Converting Reactions 1
(Conversion to ATP)

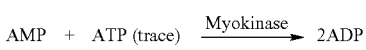
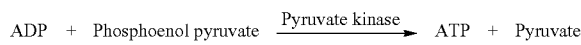

Step 3 - Detecting Reactions 1
(Fluorophotometric assay of NADPH)

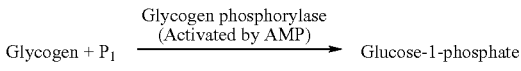

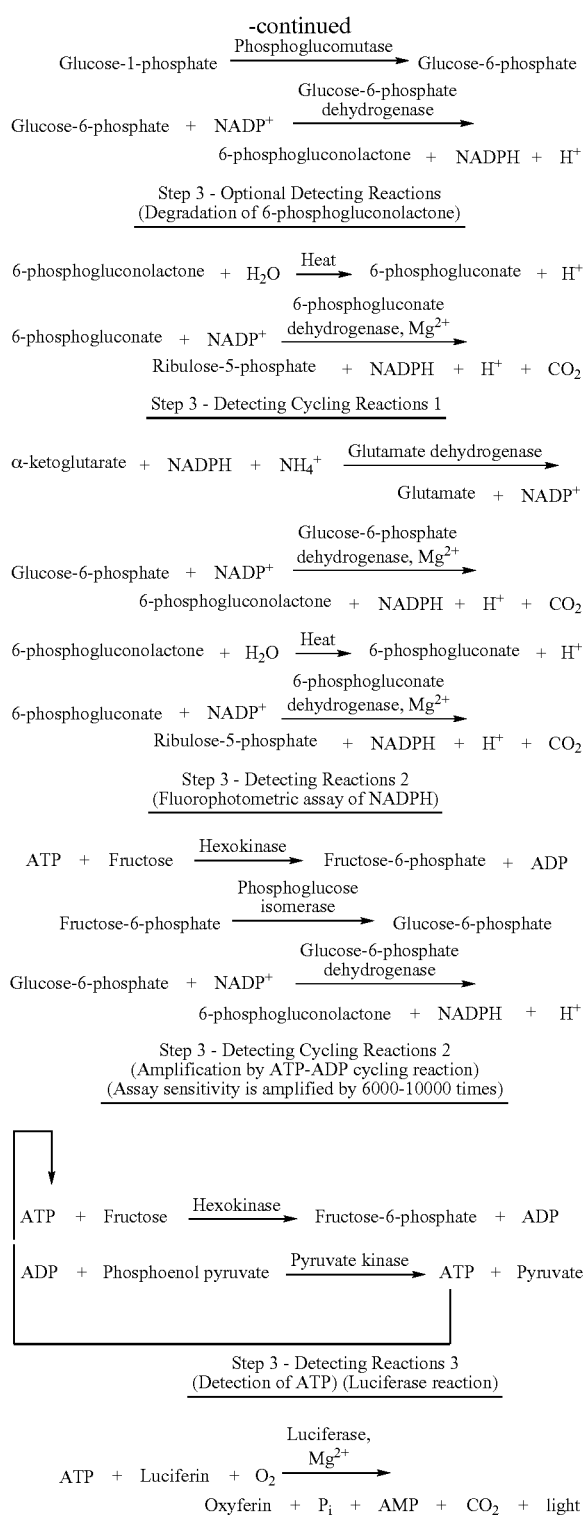

The reactions illustrated in the above schemes are further demonstrated below.

Step 1—Cleaning Reactions
(Removal of Endogenous Non-Cyclic Adenine Nucleotides and Glucose-6-Phosphate)

The present method for measurement comprises steps in which endogenous compounds having non-cyclic adenine group other than cAMP (adenosine, ATP, ADP and AMP) are enzymatically removed by a mixture of apylase, adenosine deaminase and alkaline phosphatase. Preferably, the present method comprises a step in which glucose-6-phosphate in a sample is enzymatically converted into glucose by using alkaline phosphatase (Cleaning Reactions).

The Cleaning Reactions of the present invention can remove all endogenous ATP, ADP and AMP which are present in much higher concentrations than cAMP and substantially increase the background signal. Since glucose-6-phosphate generates during subsequent Detecting Reactions, it is favorable to enzymatically remove glucose-6-phosphate from a sample previously for improving the precision of measurement. The Cleaning Reactions are important for raising sensitivity.

Also, the Cleaning Reactions period was extremely shortened and simplified by deleting 5'-nucleotidase from four kinds of enzymes, i.e. apyrase, 5'-nucleotidase, alkaline phosphatase and adenosine deaminase which have been used in a conventional cleaning reaction step. That is, it has been found that about 1 hour of the conventional cleaning reaction period can be shortened to only 5 to 10 minutes.

Step 1—Optional Cleaning Reactions 1
(Removing of Fructose-6-Phosphate)

It is favorable to remove fructose-6-phosphate, which is generated during Cycling Reactions and Detecting Reactions, from a sample previously by hydrolysis with alkaline phosphatase.

Step 1—Optional Cleaning Reactions 2
(Removal of Endogenous Glycogen in a Sample)

It is more favorable to remove from a sample endogenous glycogen, which is converted to glucose-6-phosphate by using glucose oxidase, glycogen phosphorylase and alkaline phosphatase (Optional reactions). According to this Optional Cleaning Reactions, endogenous glycogen which is an interfering substance in Detecting Reactions, wherein a known amount of glycogen is added, is destroyed.

Step 2—Converting reaction (Conversion to AMP)

Subsequently, phosphodiesterase is combined with the reaction mixture after the Cleaning Reactions so that cAMP is converted to AMP (Converting Reaction).

Step 3—Detecting Reactions
(Fluorometric Assay of NADPH)

After the Converting Reactions, glycogen and inorganic phosphoric acid are added to the reaction mixture and an amount of AMP is determined by correlating a level of glucose-6-phosphate which is finally generated from glycogen with glycogen phosphorylase activated by AMP. Glucose-1-phosphate is converted to glucose-6-phosphate with phosphoglucomutase and finally alucose-6-phosphate is enzymatically converted into 6-phosphogluconolactone, NADPH and $H^+$. The concentration of NADPH is measured by fluorometric assay, for example, according to the method of Trus et al. [M. Trus et al., *Diabetes*, 29, 1 (1980)].

Step 3—Optional Detecting Reactions
(Degradation of 6-Phosphogluconolactone)

And also, 6-phosphogluconolactone can be converted into 6-phosphogluconate by heating in an aqueous solution in vitro, and then 6-phosphogluconate can be converted into NADPH and ribulose-5-phosphate in the presence of $NADP^+$ in vitro. The concentration of NADPH can be increased by the Optional Reaction and measured by fluorometric assay, for example, according to the method of Trus et al. as described above [M. Trus et al., *Diabetes*, 29, 1 (1980)].

Where stimulated adenylate cyclase activity was measured in the same preparation from rabbit heart with both the modified Salomon radioactivity method and the present fluorometric method without alkaline phosphatase, the results were similar. Weign et al., *Anal. Biochem.*, 208, 217 (1993). Result with the radioactive assay are comparable to the present fluorometric method. Although the absolute specific activities are different when the results from the radioactive assay and the fluorometric assay are compared, the fold stimulation of adenylate cyclase as determined using either method is similar. The differences in specific activities are most likely due to minor factors in adenylate cyclase reaction mixtures. That is, unlabelled cAMP is used in the radioactive assay to prevent [$^{32}$P] cAMP degradation by endogenous phosphodiesterases, whereas theophylline is used in the fluorometric assay to inhibit endogenous phosphodiesterase degradation of newly synthesized cAMP.

Moreover, measurement of adenylate cyclase using ATP-ADP Cycling reactions as shown in Step 3—Detective Cycling Reactions 2, revealed that the absolute specific activities were the same for both the radioactive and fluorometric assays.

The method of the present invention is conveniently carried out by a kit previously prepared, and such a kit comprises vials containing enzymes, buffer solutions and the like to be used at each reaction step.

Specifically, a kit for performing a method for quickly determining the cAMP content or the adenylate cyclase activity of the present invention is exemplified by a kit which comprises (1) a vial for the cleaning reactions comprising effective amounts of apylase, alkaline phosphatase and adenosine deaminase to remove endogenous non-cyclic adenine nucleotides consisting of ATP, ADP and AMP, and endogenous glucose-6-phosphate in a biological sample; (2) a vial for the converting reaction comprising an effective amount of phosphodiesterase to enzymatically convert cAMP in the biological sample to AMP; and (3) vials for the detecting reactions comprising effective amounts of (a) glycogen, inorganic phosphoric acid and glycogen phosphorylase to convert glycogen to glucose-1-phosphate, (b) phosphoglucomutase to convert glucose-1-phosphate to glucose-6-phosphate, and (c) glucose-6-phosphate dehydrogenase and NADP(β-nicotinamide adenine dinucleotide phosphate)$^+$ to convert glucose-6-phosphate to 6-phosphogluconolactone and NADPH.

Also, another kit for performing a method for quickly determining the cAMP content or the adenylate cyclase activity of the present invention may be a kit which comprises (1) a vial for the cleaning reactions comprising effective amounts of apylase, adenosine deaminase and alkaline phosphatase to enzymatically remove endogenous non-cyclic adenine nucleotides consisting of ATP, ADP and AMP, and endogenous glucose-6-phosphate in a biological sample; (2) a vial for the converting reaction comprising effective amounts of phosphodiesterase, ATP, myokinase, phosphoenol pyruvate and pyruvate kinase to enzymatically convert cAMP in the biological sample to AMP; and (3) vials for the detecting reactions comprising effective amounts of (a) fructose and hexokinase to convert ATP to fructose-6-phosphate and (b) phosphoglucose isomerase, glucose-6-phosphate dehydrogenase and NADP$^+$ to convert fructose-6-phosphate to 6-phosphogluconolactone and NADPH.

The method of the present invention is sensitive enough to measure cAMP in small biological samples weighing less than 0.1 mg and can be adapted to measure 0.1 fmol cAMP/sample. According to the present invention, a known amount of ATP is added to a biological sample and then the ATP is converted into cAMP by action of adenylate cyclase in the sample. Adenylate cyclase activity may be provided by determining the converted AMP after removing all adenine nucleotides such as endogenous ATP by Cleaning Reactions.

Ammonium ion produced from adenosine in Cleaning Reaction drives the cleaning reaction sequence essentially to completion, preventing reformation of nucleotides in the sample. These steps provide for a significant unexpected improvement over fluorometric assays. Weign et al., *Anal. Biochem.*, 208, 217 (1993).

BEST MODE FOR CARRYING OUT THE INVENTION

Figure 1:
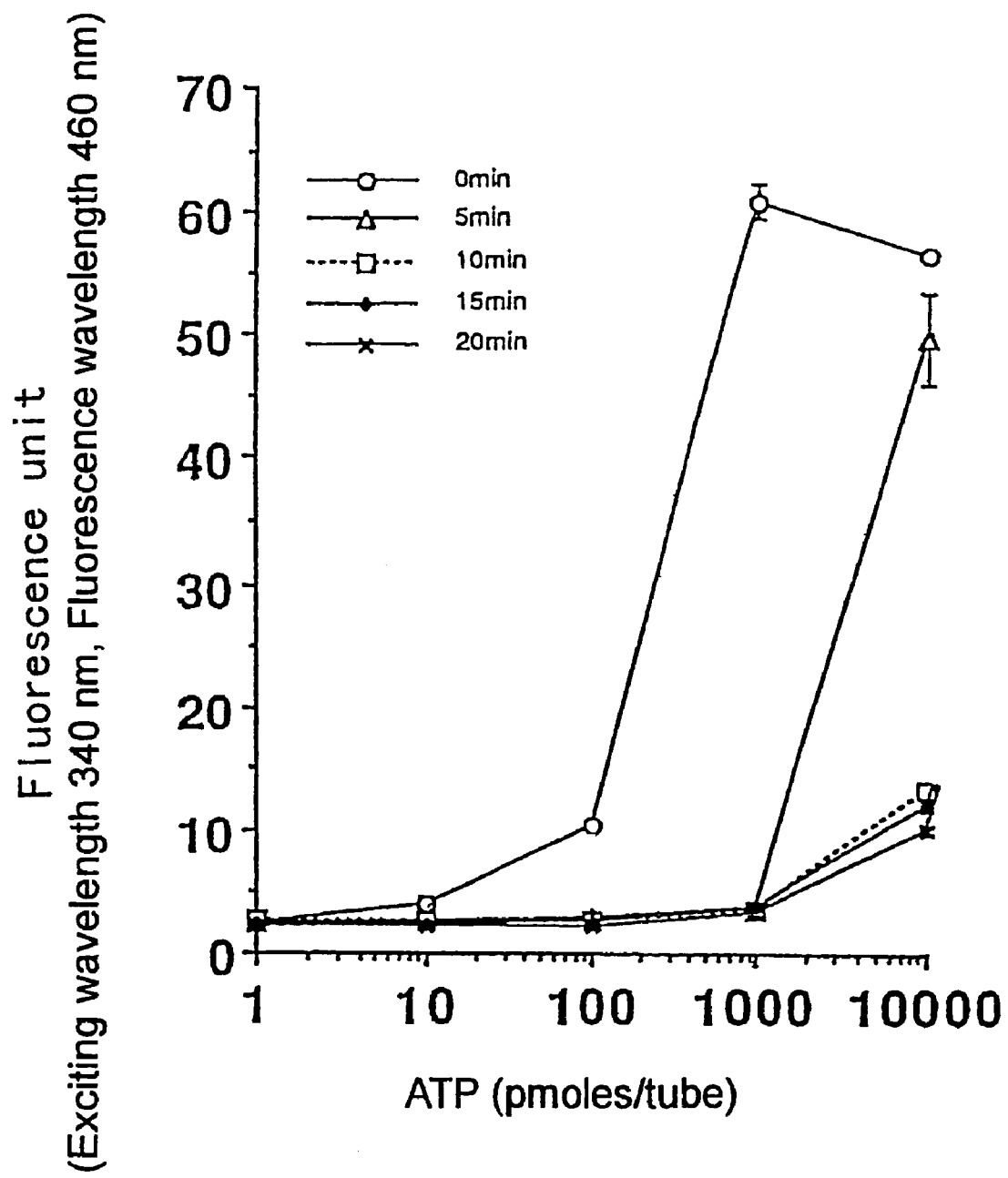
FIG. 1 is a line graph showing the fluorescence against concentration of ATP in various incubation periods.

The physiological material which is assayed with the present method is preferably obtained from a mammalian source, including tissue, blood cell, bone and physiological fluids such as urine, blood, spinal fluid and the like and may be fresh or frozen. Lowry et al., *A Flexible System of Enzymatic Analysis*, Harcourt Brace Jovanovich, New York (1972).

Thus, in a preferred embodiment, the present invention comprises the steps of:

Step 1—Cleaning Reaction (Removal of Endogenous Non-Cyclic Nucleotides and Glucose-6-Phosphate)

A sample of a physiological material comprising cAMP, glucose-6-phosphate and at least one non-cyclic adenine nucleotide, i.e., selected from the group consisting of ATP, ADP, AMP and mixture thereof is combined with an aqueous buffer comprising a mixture or apyrase, adenosine deaminase, and alkaline phosphatase so that said non-cyclic adenosine nucleotides (the ATP, ADP and/or AMP) are enzymatically converted to remove.

The wording "more quickly" means that the period of Cleaning Reaction which has conventionally taken about 1 hour is shorten within about 5 to 10 minutes, i.e., by from a twelfth to a sixth, at least a sixth of the reaction period.

Step 1—Optional Cleaning Reactions 2

And optionally, the reaction mixture is combined with a mixture of glucose oxidase and glycogen phosphorylase and alkaline phosphatase so that all glycogen in the sample is destroyed, while the cAMP is retained in the reaction mixture. These steps destroy all endogenous glycogen which is an interfering substance in Step 3—Detecting Reaction (Fluorometry of NADPH) in which a known amount of glycogen is added.

Step 2—Converting Reactions (Reaction of Conversion to AMP)

The reaction mixture is combined with phoshodiesterase, so that said cAMP is converted to AMP.

Step 3—Detecting Reactions
(Fluorometric Assay of NADPH)

Further said AMP is contacted with glycogen phosphorylase in a presence of glycogen and inorganic phosphatase so that glucose-1-phosphate is produced in the reaction mixture. Then the glucose-1-phosphate is enzymatically converted into 6-phosphogluconolactone, NADPH and H+ in said reaction mixture and the concentration of NADPH is fluorometrically measured. The concentration of NADPH is correlated with the concentration of adenylate cyclase activity, cAMP content or a concentration of AMP.

The method of determining cAMP is based on a principle that AMP produced by cleavage of 3',5'-phosphodiester bond of cAMP stimulates glycogen phosphorylase activity. That is, the amount of cAMP and adenylate cyclase activity correspond to the absorbance of NADPH finally obtained from glycogen phosphorylase activity which is activated by AMP produced from cAMP.

The correlation of a final concentration of NADPH with a concentration of AMP can be obtained, for example, by a calibration curve. See FIG. 2.

Preferably, following the Cleaning Reactions, the enzymes used in the Cleaning Reaction may be deactivated by heating.

Further preferably, following Step 1—Cleaning Reactions, a solution of phosphodiesterase, glycogen-phospholylase, glucose-1,6-diphosphate, inorganic phosphate, glycogen, NADP+, glucose-6-phosphate dehydrogenase, phosphoglucomutase and $Mg^{2+}$ is added to the reaction mixture and Steps 2 of Converting Reactions and Step 3 of Detecting Reactions 1 are carried out sequentially, in situ.

Step 3—Optional Detecting Reactions 1
(Degradation of Phosphogluconolactone)

The concentration of NADPH which is generated in Step 3 can be increased by sequentially converting the 6-phosphogluconolactone to 6-phosphogluconate by heating the reaction mixture of Step 3—Detecting Reactions 1 and then reacting the 6-phosphogluconate with added NADP+ and 6-phosphogluconate dehydrogenase in the presence of $Mg^{2+}$ to yield ribulose-5-phosphate, NADPH, H+ and $CO_2$.

Step 3—Detective Cycling Reaction 1

The effective concentration of NADPH which is generated in Step 3—Detecting Reactions 1 can be increased in orders of magnitude by employing it in cycling reaction system. One such reaction system converts NADPH added to α-ketoglutarate into NADP and glutamate. The NADPH+ in turn converts added glucose-6-phosphate into 6-phosphogluconolactione and NADPH. As described above, the 6-phosphogluconolactone can be hydrolyzed ($H_2O$, heat) and converted to ribulose-5-Phosphate and NADPH in the presence of 6-phosphogluconate dehydrogenase. Lowry et al., *A Flexible System of Enzymatic Analysis*, Harcourt Brace Jacovanovich, New York (1972).

Step 2—Optional Converting Reactions 1 (Reaction of Conversion to ATP)

Alternatively, the AMP which is produced from cAMP in Step 2—Converting Reactions can be converted to ADP by combining it with a trace amount of ATP in the presence of myokinase. The ADP which is produced is then converted to ATP and pyruvate by combining the ADP with 2-phospho (enol)pyruvate kinase. One molecular AMP produces one molecular ATP in this step (Reaction of converion to ATP).

Step 2—Converting Reactions and Step 2—Optional Converting Reactions 1, in which cAMP is converted to AMP, and AMP is converted to ATP through ADP, can be carried out sequentially at one step.

Step 3—Detecting Reactions 2
(Fluorometric Assay of NADPH)

Further, ATP is converted to fructose-6-phosphate and ADP by combining with hexokinase In the presence of fructose. Fructose-6-phosphate is converted in the presence of phosphoglucoisomerase to glucose-6-phosphate, which is enzymatically converted to 6-phosphogluconolactone, NADPH and H+. The concentration of NADPH is measured by the method of Trus et al. as described above. M. Trus et al., *Diabetes*, 29, 1 (1980).

Step 3—Optional Detecting Reactions 1

Alternatively, as described above, the 6-phosphogluconolactone can be hydrolyzed and further converted to 6-phosphogluconate, which can be converted to NADPH, H+, $CO_2$ and ribulose-5-phosphate.

Step 3—Detective Cycling Reactions 2 (Amplification of ATP-ADP Cycling Reaction)

Further, ATP is subjected to ATP-ADP cycling reaction. That is, ATP is converted to fructose-6-phosphate and ADP by combining it with hexokinase in the presence of fructose. Then the ADP is converted to ATP and pyruvate by combining phosphoenol pyruvate in the presence of pyruvate kinase. The ATP thus produced is again converted to fructose-6-phosphate and ADP. By repeating of these reactions, fructose-6-phosphate can be finally accumulated.

A chelating agent is added in order to deactivate enzymes at the end of the Cycling Reactions. The chelating agents can be exemplified by polyaminocarboxylic acid such as EDTA, oxycarboxylic acid such as citric acid, preferably, EDTA.

The resulting fructose-6-phoshate, produced from the excess fructose and phospho(enol)pyruvate used in the Cycling Reactions, is converted to glucose-6-phosphate using phosphoglucose isomerase, and the glucose-6-phosphate is converted into 6-phosphoaluconolactone and NADPH by exposing the glucose-6-phosphate dehydrogenase and NADP+. The NADPH concentration can then be determined by Trus et al. method. M. Trus et al., *Diabetes*, 29, 1 (1980). See Step 3—Detecting Reactions 2 as described above.

Step 3—Detecting Reactions 3

According to the present invention, it is possible to absorptiometrically detect the ATP produced as shown in Step 2—Optional Converting Reactions 1 with chemiluminescence assay that utilizes the lucifelase reaction and firefly lucifern. Wulff et al., *Methods of Enzymatic Analysis*, Bergmeyer H. U., eds., VCH (1985). From ATP determination, it is possible to calculate the AMP concentration and the cAMP concentration and adenylate cyclase activity corresponding to them.

Although the rate of this reaction is very slow, the yield of the reaction (defined as the ratio of the number of emitted photons and the number of converted ATP molecules) is almost 100%. The intensity of the emitted light is directly proportional to the ATP concentration and is measured at 582 nm.

If a principle of a reaction system is identical, the present method of the present invention can be adapted to determination of any substance other than AMP, for example, guanylate cyclase activity, guanosine 3',5'-cyclic monophosphate (cGMP) and guanosine 3',5'-monophosphate (GMP) by applying a suitable enzyme corresponding to GMP. The reaction schemes used are shown below.

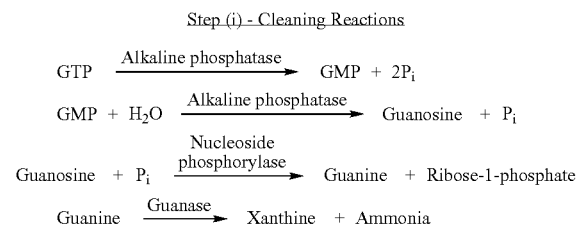

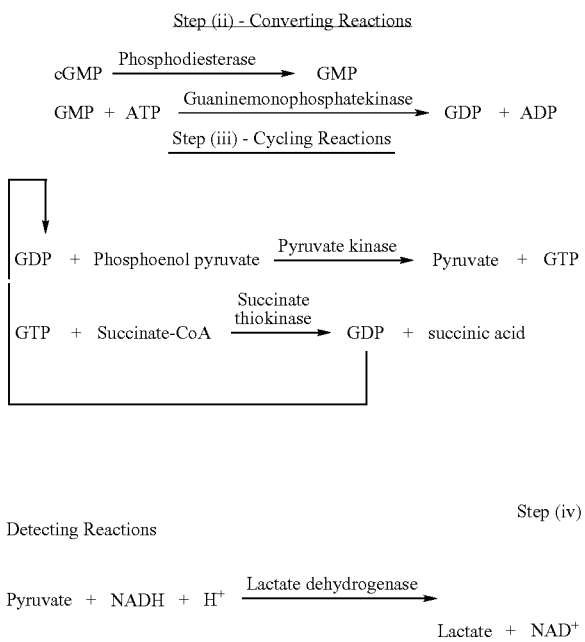

Detecting Reactions    Step (iv)

Pyruvate + NADH + H⁺ —Lactate dehydrogenase→ Lactate + NAD⁺

Step (i)—Cleaning Reaction

As described above, a cleaning mixture of alkaline phosphatase, nucleoside phosphorylase and guanase is used in the Cleaning Reactions. Alkaline phosphatase may be used to dephosphorylate compounds such as glucose-6-phosphate and non-cyclic nucleotides which may increase blank values during the measurement of cGMP (Cleaning Reactions).

In the Cleaning Reactions, GTP in a sample is converted to GMP plus 2Pi followed by conversion to guanosine and Pi. Guanosine is converted into guanine and ribose-1-posphate and guanine is converted into xanthine and ammonia. Likewise in the Cleaning Reaction for determination of cAMP, the Formation of ammonium (or $NH^{4+}$) in the final Cleaning Reactions drives the series of linked reactions essentially to completion, ensures removal of the interfering nucleotides.

Preferably, the enzymes used in the Cleaning Reaction are deactivated, e.g., by heating, prior to the next Step (ii)—Converting Reaction.

Step (ii)—Converting Reaction

The cGMP present in the sample is then converted to GMP with phosphodiesterase. The GMP is combined with ATP in the presence of guanine monophosphate kinase to yield guanosine-5'-diphosphate (GDP) and ADP.

Step (iii)—Cycling Reactions

The GDP is employed in the presence of excess PEP, succinyl-CoA and inorganic phosphate (Pi) to yield an amount of pyruvate (Cycling Reactions).

Step (iv)—Detecting Reactions

This pyruvate is quantitated indirectly by adding a known amount of NADH which in the presence of acid is converted to lactate and NAD⁺. Thus, the fluorescence of the indicator samples is decreased in direct proportion to the amount of pyruvate generated in the sample to be assayed for cGMP, GMP or guanylate cyclase. Also, in order to increase the assay sensitivity, after decomposition of excess NADH with acid, NAD⁺ formed may be converted with alkali to 2-hydroxynicotinic aldehyde having higher fluorescence intensity. K. Scya et al., Anal. Biochem., 272, 243 (1999).

According to the present invention, an alternative way to measure GMP is to measure an amount of ATP which is decomposed by guanine monophosphate kinase in Step (ii)—Converting Reaction. The amount of ATP can be determined by a known method as described above.

In addition to improving assay sensitivity, measurement of adenylate cyclase activity or guanylate cyclase activity with the present enzymatic assays is significantly less costly, less time consuming, moreover, safer for the operator and better for environment because of using no radioactive substance.

Finally, the present assay can readily be adapted to determine the amount of endogenous or exogenous phosphodiesterase in a biological sample. That is, a single, preselected amount of cAMP is added to a sample containing an unknown concentration of phosphodiesterase. Any inhibitors specific to phosphodiesterases can be added as needed. A standard curve is generated by adding a single, preselected excess amount of cAMP to different preselsected, known amounts of phosphadiesterase. After a finite amount of reaction time (5-60 minutes) in which some but not all of the added cAMP is transformed to AMP by the phosphodiesterase, the reaction is stopped. A cAMP standard curve can be run concurrently to verify that all reactions are working adequately. A cleaning reaction is initiated to degrade all non-cyclic adenine nucleotides. The remaining cAMP will be inversely proportional to the native plus added phosphodiesterase. Then cAMP is converted to AMP by a conventional method to determine.

Specifically, a tissue sample is dissolved in a SET buffer (Sucrose 0.5 M, Tris 0.03 M, EDTA 2 mM) and to the resultant mixture, the double volumes of PDE mixture (Tris 50 mM, cAMP 50 µM) is added and incubated at 37° C. for 20 minutes. The reaction mixture is heated at 80° C. for 30 minutes. Cleaning Reaction Mixture in a volume four times as much as a tissue sample is added to the reaction mixture and incubated at 37° C. for 1 hour. The reaction mixture is heated at 80° C. for 30 minutes. Converting Reaction Mixture in a volume ten times as much as a tissue sample is added to the reaction mixture and incubated for 1 hour at room temperature. The fluorescence intensity of resultant NADPH is measured using Detecting Reactions.

The present invention provides a preparation comprising enzymes or buffers to be used in a form of kit. The reaction materials of each step can be conveniently prepared in a kit, for example, such as Cleaning Reaction Mixture kit, Converting Reaction Mixture kit, Cycling Reaction Mixture kit, Detecting Reaction Mixture kit.

The enzymes used in the present invention are provided in the form of, for example, aqueous solutions, lyophilized or solid formulations in a container such as a vial, an ample made by suitable glass or plastic.

The enzymes can be dissolved in buffers, electrolyte, distilled water, or they can be separately put in different containers and can be mixed with just before use.

Additives such as preservatives, stabilizers, dye stuffs, excipients, pH regulators and the like can be suitably added.

In addition to the amplification reaction of the present invention, the assay as described in the present invention can employ appropriate automatic analyzers.

The present invention provides a novel, non-radioactive enzymatic fluorometric assay for adenylate cyclase activity and cAMP, as well as cAMP specific phosphodiesterase activity and the biological activity of the G regulatory proteins. And also it provides a non-radioactive enzymatic fluorometric assay for guanylate cyclase activity and cGMP.

The method of the present invention offers several advantages over currently available methods compared to conventional methods for measurement of adenylate cyclase activity and the like. Unlike the assays previously disclosed by Y. Salomon et al., in *Anal. Biochem.*, 58, 541 (1974) and *Adv. Cyclic Nucleotide Res.*, 10, 35 (1979), the present assay does not utilize any radioactive material. In addition, this assay is more sensitive and simpler to perform than the previous assays.

And also, according to the present invention, the reaction period in the method can be extremely shortened and the operation becomes simpler compared to a method which previously developed by the inventor and others. See A. Sugiyama et al., *Anal. Biochem.*, 218, 20 (1994); A. Sugiyama et al., *J. Clin. Lab.*, 8, 437 (1994); A. Sugiyama et al., *Anal. Biochem.*, 225, 368 (1995); A. Sugiyama et al., *Yamanashi Med. J.*, 10, 11 (1995). In addition, a problem of cloudy in a sample, which is not avoidable in conventional methods, is solved by using a chelating agent such as EDTA. And cAMP content in a biological sample in of order of μg can be correctly measured on a level of pmol or fmol.

The Cleaning Reaction of the present invention can remove all endogenous ATP, ADP and AMP which are present in a far higher concentration than cAMP and would otherwise substantially increase the blank. Additionally, the Cleaning Reactions can remove all endogenous glucose-6-phosphate and glycogen as interfering substances in the sample. These Cleaning Reactions are important for improving assay sensitivity.

It has been found that the reaction period of 1 hour by conventional methods could be significantly shortened to about 5-10 minutes by deletion of 5'-nucleotidase from four enzymes, i.e., apyrase, 5'-nucleotidase, alkaline phosphatase and adenosine deaminase which have been used in the conventional cleaning reactions.

After Cycling Reactions, since $Mg^{2+}$ is trapped by a chelating agent and excess of enzymes are deactivated without heating, the sample does not get cloudy.

The sensitivity of this assay can also be increased by reducing the reaction volumes. It can also be increased further by varying the concentrations of glycogen and inorganic phosphate in the reaction mixture, as reported by Meinrich et al. and E. Helmrich et al., *Biochemistry*, 52, 647 (1964). According to the present invention, measurement of adenylate cyclase activity is possible in mammalian tissue biopsy samples comprising as little as 10.0 μg of membrane protein.

Unlike the radioactive methods, where sensitivity is limited by the specific activity of $[\alpha\text{-}^{32}P]$ cAMP and the volume size for chromatographic separation and the like, there are no significant barriers to further increasing the sensitivity of the present fluorometric method. For example, cAMP has been measured over a broad concentration range of 1 fmol-1 mmol.

EXAMPLES

The invention will be further described by reference to the following detailed examples wherein the enzymes, substrates and cofactors used were obtained from Boehringer Mannheim Co., except for apyrase and 5'-nucleotidase which were from Sigma Co., St. Louis, Mo. The $[\alpha^{-32}P]$ ATP, $^3$H-cAMP, and Aquasol scintillation cocktail were purchased from New England Nuclear. Neutral Chromatographic Alumina WN-3 was obtained from Bio-Rad.

Example 1

Determination of Cleaning Reaction Period

A volume of 3 μL of ATP standard (0, 10, 100, 1000 and 10000 pmol/tube) was added into a 10×57 Pyrex® assay tube. While at room temperature, 25 μL of Cleaning Reaction Mixture (100 mM Tris-HCl, pH 8.0; 2 mM $MgCl_2$; 2 U/mL apyrase; 10 U/mL adenosine deaminase; 40 U/mL alkaline phosphatase) was added to each assay tube. The mixture was incubated at 37° C. for 0, 5, 10, 15 and 20 minutes. Then Step 2—Converting Reactions (Conversion to AMP), Optional Converting Reactions (Conversion to ATP), Step 3—Detecting Cycling Reactions 2 were sequentially carried out and an fluorescence intensity at 340 nm was measured to determine an incubation period when ATP have completely disappeared. The results are shown in FIG. 1. From the results, it was found that an interfering substance, i.e., ATP, substantially disappeared after at most 10 minutes of incubation.

Comparing Example

This test was carried out in order to compare Cleaning Reactions of the present invention with that of the cleaning reactions containing 5'-nucleotidase.

Preparation of a Cleaning Reaction Mixture Containing 5'-Nucleotidase

Tris-HCl (pH 8.0), $MgCl_2$, 5'-nucleotidase, Apyrase, Adenosine deaminase and Alkaline phosphatase were mixed and to the mixture water was added up to total 25 μL. The cleaning reaction mixture having final concentrations as shown in Table 1 was prepared

TABLE 1

A cleaning reaction mixture containing 5'-nucleotidase

| Compound | Final Reaction Concentration |
|---|---|
| Tris-HCl pH 8.0 | 100 mM |
| $MgCl_2$ | 2 mM |
| 5'-nucleotidase | 2.5 U/mL |
| Apyrase | 2 U/mL |
| Adenosine deaminase | 10 U/mL |
| Alkaline phosphatase | 20 U/mL |
| Water | up to a total volume 25 μL |

The cleaning reactions can be shown in the following reaction schemes.

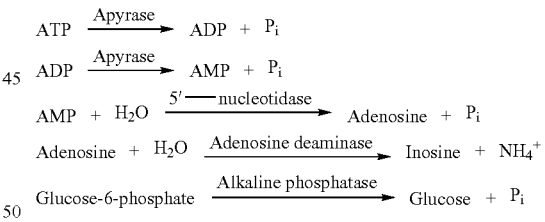

Determination of the Cleaning Reaction Period

Cleaning reactions were carried out using the cleaning reaction mixture prepared above as described in Example 1.

A volume of 3 μL of ATP standard (0, 10, 100, 1000 and 10000 pmol/tube) was added into a 10×57 Pyrex® assay tube. While at room temperature, 25 μL of the cleaning reaction mixture (100 mM Tris-HCl, pH 8.0; 2 mM $MgCl_2$; 2 U/mL apyrase; 2.5 U/mL 5'-nucleotidase; 0.1 U/mL adenosine deaminase; 20 U/mL alkaline phosphatase) was added to each assay tube. The mixture was incubated at 37° C. Then Step 2—Converting Reactions, Cycling Reactions and Detecting Reactions as described in Example 2 below were carried out and an absorbance at 340 nm was measured to determine an incubation period when ATP have completely disappeared. As the results, it was found that ATP had completely disappeared after about 1 hour of incubation.

Example 2

Micro cAMP measurement in Tissue Cultures with Enzymatic Fluorometric Assay (1) Preparation of Samples and Reaction Mixtures A. Preparation of Biological Samples (Ventricular Myocyte Preparation)

Isolated ventricular myocytes were obtained from hearts of 1 day-old rats, grown in primary cultures. There were approximately 5 million viable myocardial cells per heart. After plating at a density of approximately 1 million cells per 100 mm, dish cells were grown in minimum essential medium with Hanks balanced salt solution containing 5% bovine calf serum cells. Simpson et al., *Cir. Res.*, 51, 787 (1982). On day 4, the medium was changed. The cultures contained >90% myocardial cells and cell numbers were constant over time. Simpson et al., *Cir. Res.*, 51, 787 (1982); Rocha-Singh et al., *J. Clin. Invest.*, 88, 204 (1991); and Rocha-Singh et al., *J. Clin. Invest.*, 88, 706 (1991)

Six plates of myocytes were randomized into two groups (n=3 plates/group). The phosphodiesterase inhibitor 3-isobutyl-1-methylxanthine (IBMX) was added to the medium of each group to achieve a 2 μM final concentration. After 5 minutes, isoproterenol was added to the stimulated group to achieve a final 1 μM concentration, while the control group received no additional drug. After 5 minutes, cells from all six plates and plates of culture medium without cells were eluted with a total of 5 mL of 100% ethanol. One-tenth of the eluent (0.5 mL) from each dish was removed and air dried in a 12×75 mm borosilicate glass tube and stored at −80° C. The other 4.5 mL were similarly air dried and stored. At the time of assay, the pellet was thawed and resuspended in 100 μL of 0.5 N perchloric acid. The extracts were stirred at 4° C. for 2 minutes and sonicated for 1 minute using a sonicator (Branson Cleaning Equipment Co. A Smith-Kline Co., USA). The extract was neutralized with 25 μL of 2N KOH, centrifuged at 2000 g for 30 minutes and 80 μL of supernatant was removed for assay.

B. Preparation of Cleaning Reaction Mixture (See Step 1—Cleaning Reactions)

One molar Tris-HCl (pH 8.0) 400 μL; 0.2 mM MgCl$_2$ 40 μL; 500 U/mL apyrase 32 μL; 400 U/mL adenosine deaminase 100 μL; 4000 U/mL alkaline phosphatase 4 μL were mixed and to the mixture water was added up to a total volume 4 mL to prepare Cleaning Reaction Mixture (Table 2)

TABLE 2

Cleaning Reaction Mixture

| Compound | Final Reaction Concentration |
| --- | --- |
| Tris-HCl pH 8.0 | 100 mM |
| MgCl$_2$ | 2 mM |
| Apyrase | 4 U/mL |
| Adenosine deaminase | 10 U/mL |
| Alkaline phosphatase | 40 U/mL |
| Water | up to a total volume 4 mL |

After cooling rat ventricular myocyte preparation prepared in Example 2 (1) on ice, 0.4 μL of Reaction Mixture of Step 1—Optional Cleaning Reaction (100 mM Tris-HCl, pH 8.0; 3 mM MgCl$_2$ 3 U/mL apyrase; 150 μg/mL adenosine deaminase; 30 U/mL alkaline phosphatase and 75 μg/mL glycogen Phosphorylase-α) was added to the preparation to remove all endogenous adenine nucleotides, glycogen and glucose-6-phosphate. After incubation at 37° C. for 1 hour, enzymes were deactivated by heating at 80° C. for 30 minutes.

C. Preparation of Converting Reaction Mixture (See Step 2—Converting Reactions and Step 2—Optional Converting Reactions)

One molar Tris-HCl (pH 8.0) 400 μL, 0.2 mM MgCl$_2$ 40 μL, 4% bovine Serum Albumin 10 μL, 1 M KCl 600 μL, 0.01 M dithiothreitol 80 μL, 0.1 μM ATP 16 μL, 0.5 M Mphosphoenol-pyruvate 24 μL, 2 U/mL Phosphodiesterase 24 μL, 720 U/mL Myokinase 24 μL and 2000 U/mL Pyruvate kinase 160 μL were mixed and to the mixture water was added up to a total volume 4 mL to prepare Converting Reaction Mixture (Table 3).

TABLE 3

Converting Reaction Mixture

| Compound | Final Reaction Concentration |
| --- | --- |
| Tris-HCl pH 8.0 | 100 mM |
| MgCl$_2$ | 2 mM |
| Bovine Serum Albumin | 0.01% |
| KCl | 150 mM |
| Dithiothreitol | 2 mM |
| ATP | 40 nM |
| Phosphoenolpyruvate | 3 mM |
| Phosphodiesterase | 12 mU/mL |
| Myokinase | 4.5 U/mL |
| Pyruvate kinase | 80 U/mL |
| Water | up to a total volume 4 mL |

D. Preparation of Cycling Reaction Mixture (See Step 3—Detective Cycling Reactions 2)

One molar Tris-HCl (pH 8.0) 400 μL, 0.2 mM MgCl$_2$ 40 μL, 4% bovine Serum Albumin 10 μL, 0.1 M Fructose 30 μL, 1500 U/mL Hexokinase 160 μL were mixed and to the mixture water was added up to a total volume 4 mL to prepare Cycling Reaction Mixture (Table 4).

TABLE 4

Cycling Reaction Mixture

| Compound | Final Reaction Concentration |
| --- | --- |
| Tris-HCl pH 8.0 | 100 mM |
| MgCl$_2$ | 2 mM |
| Bovine Serum Albumin | 0.01% |
| Fructose | 3 mM |
| Hexokinase | 60 mM |
| Water | up to a total volume 4 mL |

E. Preparation of Detecting Reaction Mixture (See Step 3—Detecting Reaction 2)

One molar Tris-HCl (pH 8.0) 2000 μL, 0.2 mM EDTA 320 μL, 0.1 M NADP$^+$ 120 μL, 3500 U/mL Phosphoglucose isomerase 6 μL, 1750 U/mL Glucose-6-phosphate dehydrogenase 6 μL were mixed and to the mixture water was added up to a total volume 4 mL to prepare Cycling Reaction Mixture (Table 5).

TABLE 5

Detecting Reaction Mixture

| Compound | Final Reaction Concentration |
| --- | --- |
| Tris-HCl pH 8.0 | 100 mM |
| EDTA | 3.2 mM |
| NADP$^+$ | 0.01% |
| Phosphoglucose isomerase | 1 U/mL |
| Glucose-6-phosphate dehydrogenase | 0.5 U/mL |
| Water | up to a total volume 4 mL |

(2) Micro cAMP measurement in Tissue Cultures with Enzymatic Fluorometric Assay

According to Enzymatic Fluorometric assay comprising a series of Cleaning Reactions, Converting Reactions, Cycling Reactions and Detecting Reactions, cAMP in the ventricular myocyte preparation prepared in (A) as a sample was measured.]

1) Cleaning Reactions
(Step 1—Cleaning Reactions)

A volume of 3 μL of neutralized myocyte extract (either 2.4% or 0.24% of total eluent from 100 mm plate) or 3 μL of ATP standard (0, 3.6, 7.2, 14.4, 21.6 and 28.8 pmol/20 μL) was added into a 10×57 Pyrex® assay tube (Iwaki glass Co.). While at room temperature, 25 μL of Cleaning Reaction Mixture prepared from (B) (100 mM Tris-HCl, pH 8.0; 2 mM $MgCl_2$; 2 U/mL apyrase; 10 U/mL adenosine deaminase; 40 U/mL alkaline phosphatase) was added to each assay tube. The mixture was incubated at 37° C. or 10 minutes. Enzymes were then deactivated by heating for 30 minutes at 90° C. An internal tissue blank control was similarly prepared.

2) Converting Reactions
(Step 2—Converting Reactions (conversion to AMP) and —Optional Converting Reactions (Conversion to ATP))

A volume of 25 μL of the Converting Reaction Mixture prepared from (C) (100 mM Tris-HCl, pH 8.0; 2 mM $MgCl_2$; 0.01% bovine Serum Albumin; 150 mM KCl; 2 mM dithiothreitol; 40 nM ATP; 3 mM phosphoenol-pyruvate; 12 U/mL phosphodiesterase; 4.5 U/mL mvokinase; and 80 U/mL Pyruvate kinase) was added to each assay tube from Cleaning Reactions. The mixture was incubated at room temperature overnight. The reactions were terminated by heating the assay tubes at 90° for 5 minutes.

3) Cycling Reactions
(Step 3—Detecting Cycling Reactions 2)

A volume of 25 μL of the Cycling Reaction Mixture prepared from (D) (100 mM Tris-HCl (pH 8.0); 2 mM $MgCl_2$; 0.01% bovine Serum Albumin; 3 mM Fructose; 60 U/mL Hexokinase) was added to each assay tube from Converting Reactions. In view of the high concentrations of enzymes per reaction, it was important to set up these reactions at 0° C. to insure the same starting time for all assay tubes. The mixture was incubated at 37° C. for 2 hours (about 4000-10000 cycles).

4) Detecting Reactions
(Step 3—Detecting Reactions 2)

A volume of 125 μL of the Detecting Reaction Mixture prepared from (E) (100 mM Tris-HCl, pH 8.0; 3.2 mM EDTA; 0.6 mM $NADP^+$; 1 U/mL Phosphoglucose isomerase; 0.5 U/mL Glucose-6-phosphate dehydrogenase) was added to each assay tube from Cycling Reactions. After 20 minutes at room temperature, the final concentration of NADPH was measured using a fluorometer (Optical Technology Devises, Inc., NY). The fluorometer was set such that a reading of 10 fluorometric units was equivalent to 1 nmol of NADPH in 900 μL of buffer (50 mM Tris-HCl, pH 8.0).

Individual assay steps were verified by concurrently assaying internal controls using known concentrations of the appropriate substrate, for example, additional ATP was used to check Cleaning Reactions, an AMP standard curve was used to assess Converting Reactions and an ATP standard curve was used to assess Cycling Reactions.)

5) Results

Figure 2:
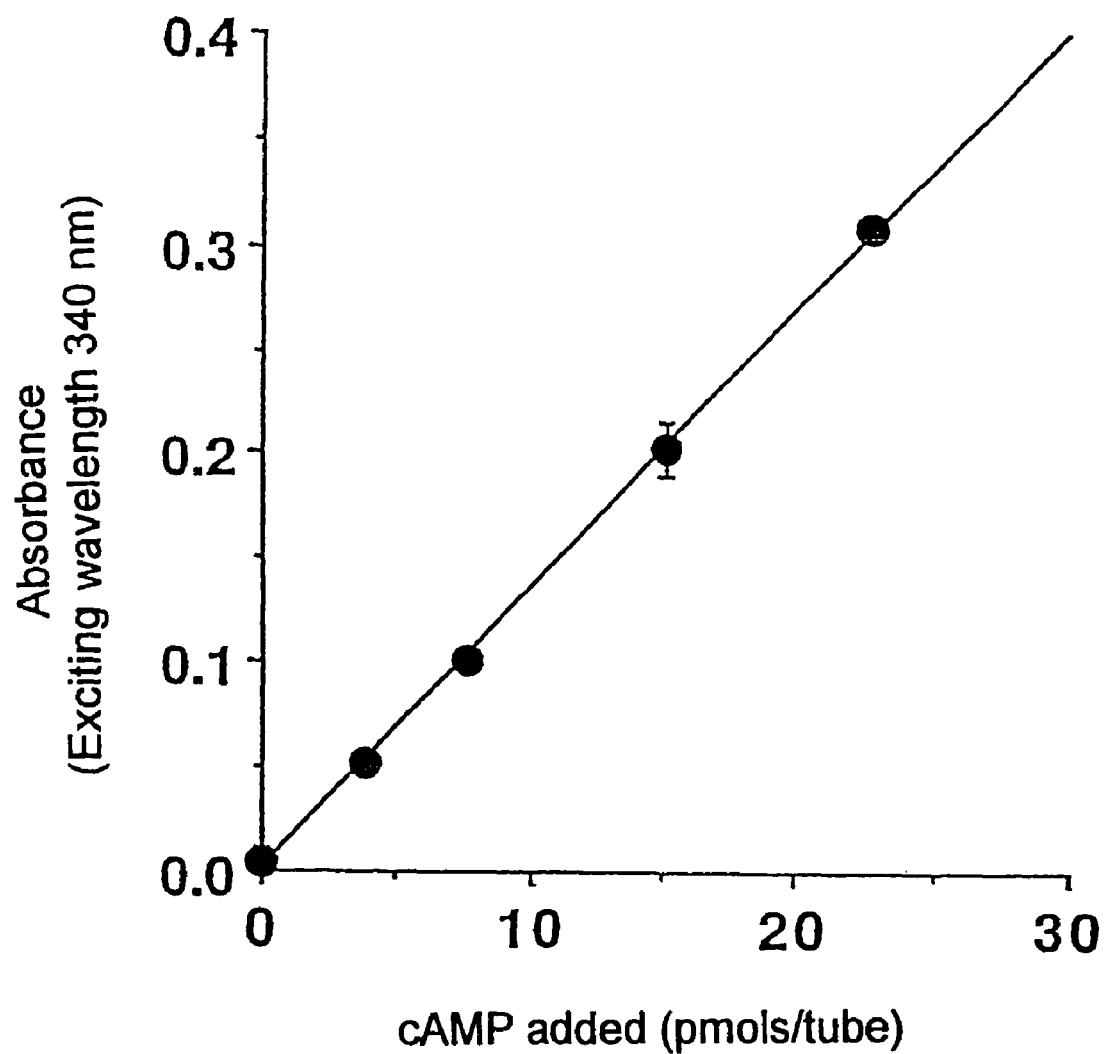
FIG. 2 is a graphical plot of the absorbance against concentration of standard samples of cAMP as determined by an embodiment of the invention.

Measurement of the absorbance from cAMP standard (0, 3.6, 7.2, 14.4, 21.6 and 28.8 pmol/20 μL) at 340 nm afforded the cAMP standard curve shown in FIG. 2.

cAMP values of control group received no additional drug and isoproterenol-stimulated cells from (1) (A) were measured for one-tenth of the eluent from each plate of cells using the cAMP standard curve (FIG. 2) to give an actual value of cAMP 680 pmol/100 mm plate.

Figure 3:
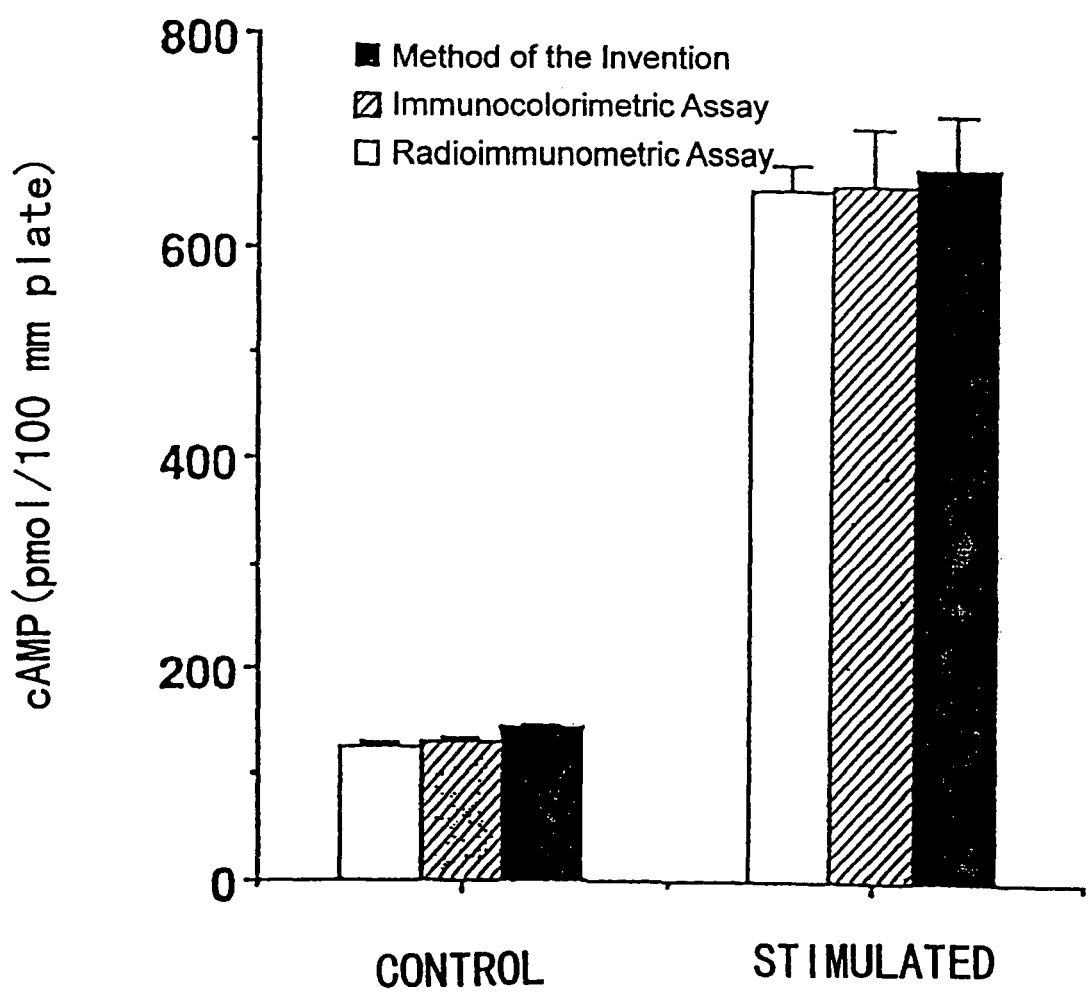
FIG. 3 is a histogram showing the amounts of cAMP detected in untreated and stimulated cells as determined by the present fluorometric method (solid) and commercially available immunocolorimetric assay (shaded) and radioimmunometric assay (clear).

The results of measurement of cAMP content using the fluorometric assay of the present invention, immunocolorimetric assay (Amersham International Co.) and radioimmunoassay (Amersham International Co.) were shown in FIG. 3. The data generated from measurements of cAMP are sufficiently coincident with the data obtained from a commercially available radioactive assay with variability usually less than 5%.

Figure 4:
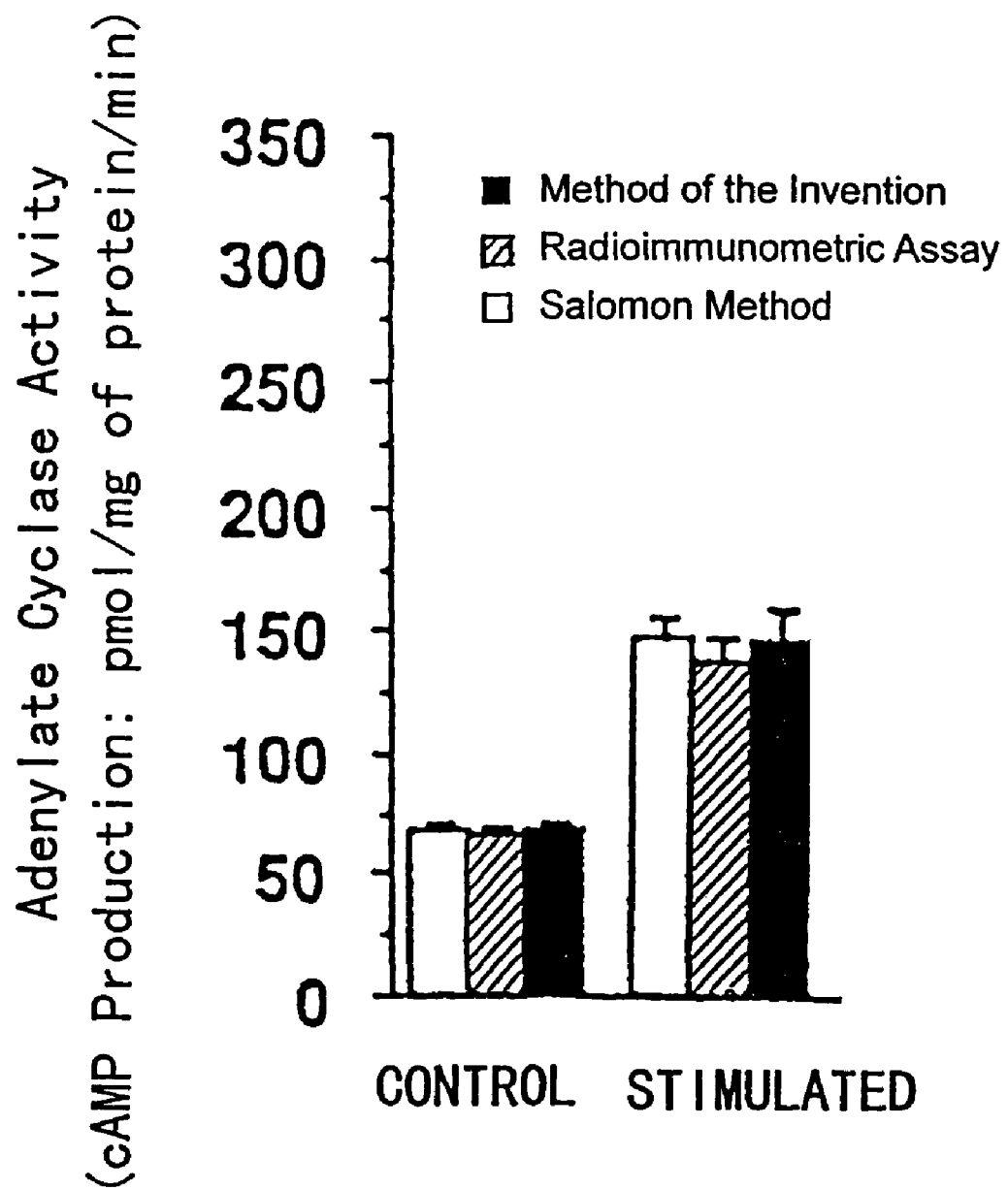
FIG. 4 is a histogram showing the adenylate cyclase activity determined by the present fluorometric method (solid) and commercially available radioimmunometric assay (shaded) and Salomon method (clear).

In addition, adenylate cyclase activity were measured from the results of quantitative measurement of cAMP using the assay of the present invention, radioimmunoassay and Salomon method. The data from three methods were shown in FIG. 4. The values of adenylate cyclase activity are assessed by cAMP amounts (pmol) per minute generated from protein 1 mg.

Example 3

Each appropriate amount of 1 M Tris-HCl pH 8.0, 0.2 mM $MgCl_2$, 1 M $K_2HPO_4$, 0.1 mM AMP, 4000 U/mL alkaline phosphatase, and 10 mg/mL glycogen phosphorylase were mixed and to the mixture water is added to prepare Cleaning Reaction Mixture in final concentrations as shown below.

TABLE 6

| Cleaning Reaction Mixture | |
|---|---|
| Compound | Final Reaction Concentration |
| Tris-HCl pH 8.0 | 100 mM |
| $MgCl_2$ | 2 mM |
| $K_2HPO_4$ | 5 mM |
| AMP | 0.1 mM |
| Alkaline phosphatase | 20 U/mL |
| Glycogen phosphorylase | 10 μg/mL |
| Water | — |

Each appropriate amount of 1 M Tris-HCl (pH 8.0), 0.1 mM $MgCl_2$, 1 M $K_2HPO_4$, 0.1 M AMP, 0.1 M dithiothreitol, 1 mM glucose-1,6-diphosphate, 4% bovine Serum Albumin, 0.1 M NADP, and 10 mg/mL Glycogen phosphorylase, 10 mg/mL phosphoglucomutase, and 5 mg/mL Glucose-6-phosphate dehydrogenase were mixed and to the mixture water is added to prepare Converting Reaction Mixture in final concentrations as shown below.

TABLE 7

| Converting Reaction Mixture | |
|---|---|
| Compound | Final Reaction Concentration |
| Tris-HCl pH 8.0 | 100 mM |
| $MgCl_2$ | 2 mM |
| $K_2HPO_4$ | 5 mM |
| AMP | 0.1 mM |
| Dithiothreitol | 1 mM |
| Glucose-1,6-diphosphate | 4 μM |
| Bovine Serum Albumin | 0.01% |
| NADP | 0.2 mM |
| Glycogen phosphorylase | 20 μg/mL |
| Phosphoglucomutase | 4 μg/mL |
| Glucose-6-phosphate dehydrogenase | 2 μg/mL |
| Water | — |

1) Cleaning Reactions
(Step 1—Optional Cleaning Reactions 2)

An aqueous glycogen solution comprising 206 μM of glycogen was prepared and distributed into 12 Pyrex® assay tubes (Iwaki Glass Co., 10×57 mm), each three tubes in an amount of 0, 20, 40 and 80 μL, and water was added to each assay tube up to a total volume 80 μL. At room temperature, 500 µL of Cleaning Reaction Mixture (100 mM Tris-HCl, pH 8.0; 2 mM $MgCl_2$; 5 mM $K_2HPO_4$; 0.1 mM AMP; 20 U/mL Alkaline phosphatase; and 10 µg/mL Glycogen phosphorylase) was added to each assay tube. The mixture were incubated at 37° C. for 60 minutes.

2) Detecting Reactions (Step 3—Detecting Reactions 1)

A volume of 500 µL of the converting Reaction Mixture (100 mM Tris-HCl, pH 8.0; 2 mM $MgCl_2$; 5 mM $K_2HPO_4$; 0.1 mM AMP; 1 mM dithiothreitol, 4 µM glucose-1,6-diphosphate, 0.01% bovine Serum Albumin, 0.2 mM NADP, and 20 µg/mL glycogen phosphorylase, 4 µg/mL phosphoglucomutase and 2 µg/mL glucose-6-phosphate dehydrogenase) was added to each assay tube. The mixture was incubated at 37° C. for 30 minutes. The fluorescence wavelength of 460 nm for each assay tube was measured at a exiting wavelength of 340 nm. In result, the data confirmed that glycogen in the glycogen solution was completely removed by the Cleaning Reactions.

Example 4

Preventive Effect Against Clouding by Chelate Agents

A volume of 125 µL of Detecting Reaction Mixture without EDTA (100 mM Tris-HCl, pH 8.0; 0.6 M $NADP^+$; 1 U/mL Phosphoglucose isomerase, 0.5 U/mL Glucose-6-phosphate dehydrogenase) was added to the assay tube after Cycling Reactions in Example 2. The mixture was incubated at 90° C. for 30 minutes and the enzymes were deactivated. Clouding in the assay solution was surveyed with eyes. The solution from Example 2 to which was added Detecting Mixture with EDTA was employed as a control. The enzymes in the control were deactivated by EDTA at room temperature.

In result, while the control was clear, the mixture deactivated by heating got cloudy.

INDUSTRIAL APPLICABILITY

The present invention provides a method of determining cAMP content or an adenylate cyclase activity in a biological sample without the use of radioactive agents.

That is, the cleaning reactions according to the present invention can remove selectively and efficiently endogenous non-cyclic adenine nucleotides such as ATP, ADP and AMP, and glucose-6-phosphate, which act as interfering substances in assay of cAMP. After conversion of cAMP in a sample into AMP, AMP is enzymatically converted into ATP. ATP is then converted via fructose-6-phosphate into glucose-6-phosphate in order to obtain NADPH, the concentration of NADPH is finally determined by a fluorometric method. By the correlation with a final concentration of NADPH, a cAMP content or adenylate cyclase activity can be safely obtained only by enzymatic or chemical reactions without the use of radioactive agents.

In particular, according to the present invention, the enzymes used in the cleaning reactions are limited to apyrase, alkaline phosphatase and adenosine phosphatase. Also, by adjustment of their concentrations, the present invention succeeds in making the processes for determination become much simpler and in making their reaction periods be extremely shortened within about 5 to 10 minutes, i.e., by from a twelfth to a sixth compared to conventional methods.

Since the cAMP content depends on eutrophy, proliferation, differentiation, adaptation of cells and changes in sensitivity, measurement of cAMP provides a useful way to assess cell viability, endocrine hormonal axis function, adenylate cyclase activity and phosphodiesterase activity. Therefore, the value of cAMP content can be an excellent index in the fields of basic and clinical medicine.

According to the method of the present Invention, cAMP content and adenylate cyclase activity corresponding to cAMP can be determined safely and in high sensitivity.

The invention claimed is:

1. A kit for determining cAMP content or an adenylate cyclase activity in a biological sample which comprises:
    (1) a vial for Cleaning Reaction comprising effective amounts of apyrase, alkaline phosphatase and adenosine deaminase without 5'-nucleotidase to remove non-cyclic adenine nucleotides consisting of endogenous ATP, ADP and AMP, and endogenous glucose-6-phosphate in a biological sample;
    (2) a vial for Converting Reaction comprising an effective amount of phosphodiesterase to enzymatically convert cAMP in a biological sample into AMP; and
    (3) a vial for Detecting Reaction comprising glycogen, inorganic phosphoric acid and glycogen phosphorylase to convert glycogen into glucose-1-phosphoric acid; phosphoglucomutase to convert glucose-1-phosphate into glucose-6-phosphate; and glucose-6-phosphate dehydrogenase and $NADP^+$ to convert glucose-6-phosphate into 6-phosphogluconolactone and NADPH.

2. A kit for determining cAMP content or adenylate cyclase activity in a biological sample which comprises:
    (1) a vial for Cleaning Reaction comprising effective amounts of apyrase, alkaline phosphatase and adenosine deaminase without 5'-nucleotidase to enzymatically remove endogenous non-cyclic adenine nucleotides other than cAMP, and endogenous glucose-6-phosphate in a biological sample;
    (2) a vial for Converting Reaction comprising effective amounts of phosphodiesterase, ATP, myokinase, phosphoenolpyruvic acid and pyruvate kinase to enzymatically convert cAMP in the biological sample into ATP; and
    (3) a vial for Detecting Reaction comprising fructose and hexokinase to convert ATP into fructose-6-phosphate; phosphoglucose isomerase, glucose-6-phosphate dehydrogenase and $NADP^+$ to convert fructose-6-phosphate into 6-phosphogluconolactone and NADPH.

* * * * *